United States Patent
Winekoff

(10) Patent No.: US 6,871,648 B1
(45) Date of Patent: Mar. 29, 2005

(54) OXYGEN AND INHALATION MEDICATION DELIVERY SYSTEM

(76) Inventor: Mark C. Winekoff, 8610 Santa Rosa Rd., Atascadero, CA (US) 93422

( * ) Notice: Subject to any disclaimer, the term of this patent is extended or adjusted under 35 U.S.C. 154(b) by 32 days.

(21) Appl. No.: 10/640,461

(22) Filed: Aug. 12, 2003

Related U.S. Application Data

(60) Provisional application No. 60/402,572, filed on Aug. 12, 2002.

(51) Int. Cl.$^7$ .......................... A63B 7/10; A61M 11/00
(52) U.S. Cl. .......................... 128/205.13; 128/200.14; 128/200.21; 128/203.28; 128/203.29; 128/207.12
(58) Field of Search ...................... 128/200.14, 200.19, 128/200.21, 200.22, 203.16, 203.28, 203.29, 204.11, 204.12, 204.28, 205.13, 205.14, 205.17, 207.12; 239/338

(56) References Cited

U.S. PATENT DOCUMENTS

| | | | | | |
|---|---|---|---|---|---|
| 2,678,044 A | * | 5/1954 | Szekely et al. | ........ | 128/200.18 |
| 3,301,255 A | * | 1/1967 | Thompson | ............ | 128/200.18 |
| 3,580,249 A | * | 5/1971 | Takaoka | ................ | 128/200.14 |
| 3,667,463 A | * | 6/1972 | Barnes | .................. | 128/203.16 |
| 3,769,973 A | * | 11/1973 | Esbenshade, Jr. | ...... | 128/200.14 |
| 4,598,704 A | * | 7/1986 | Bordoni et al. | ........ | 128/200.14 |
| 4,649,912 A | * | 3/1987 | Collins | .................. | 128/202.13 |
| 4,865,027 A | * | 9/1989 | Laanen et al. | ......... | 128/200.21 |
| 4,886,055 A | * | 12/1989 | Hoppough | ............. | 128/200.14 |
| 4,938,209 A | * | 7/1990 | Fry | ........................ | 128/200.21 |
| 5,099,833 A | * | 3/1992 | Michaels | ............... | 128/200.14 |
| 5,119,807 A | * | 6/1992 | Roberts et al. | ........ | 128/200.24 |
| 5,143,061 A | * | 9/1992 | Kaimer | ................... | 128/206.24 |
| 5,277,175 A | * | 1/1994 | Riggs et al. | ........... | 128/200.21 |
| 5,357,945 A | * | 10/1994 | Messina | ................ | 128/200.14 |
| 5,586,551 A | * | 12/1996 | Hilliard | ................. | 128/203.29 |
| 5,701,886 A | * | 12/1997 | Ryatt | ..................... | 128/203.12 |
| 5,762,063 A | * | 6/1998 | Coates et al. | .......... | 128/205.13 |
| 5,996,579 A | * | 12/1999 | Coates et al. | .......... | 128/205.13 |
| 6,328,030 B1 | * | 12/2001 | Kidwell et al. | ........ | 128/200.21 |
| 6,340,023 B2 | * | 1/2002 | Elkins | ................... | 128/200.21 |

* cited by examiner

Primary Examiner—Henry Bennett
Assistant Examiner—Mital Patel

(57) ABSTRACT

A medication inhalation therapy apparatus designed for the delivery of finely misted medicines to a patient in conjunction with the inhalation of 100% oxygen by the patient. The apparatus comprises a facemask equipped with an oxygen port for delivering oxygen, the facemask placed about or on the face of the patient. The facemask has a nebulizer mechanism disposed thereon, which is used to deliver medication in addition to oxygen. The nebulizer mechanism comprises a nebulizer port, which rotates 90 degrees in either direction to allow the present invention to be used in various angles. The nebulizer port is adapted to receive a nebulizer head, wherein are placed inhaleable medications, which are nebulized. When the apparatus is used for medication inhalation therapy, the nebulizer head receives oxygen for nebulizing inhaleable medications placed therein, the oxygen received from an oxygen port, which delivers oxygen to the facemask. When the apparatus is not being used for medication inhalation therapy, the nebulizer head is disconnected from the oxygen port. The apparatus may also be provided with a horizontal bag, which permits flow of oxygen to a patient, wherein the flow is unimpeded by objects placed upon the patient's chest.

19 Claims, 2 Drawing Sheets

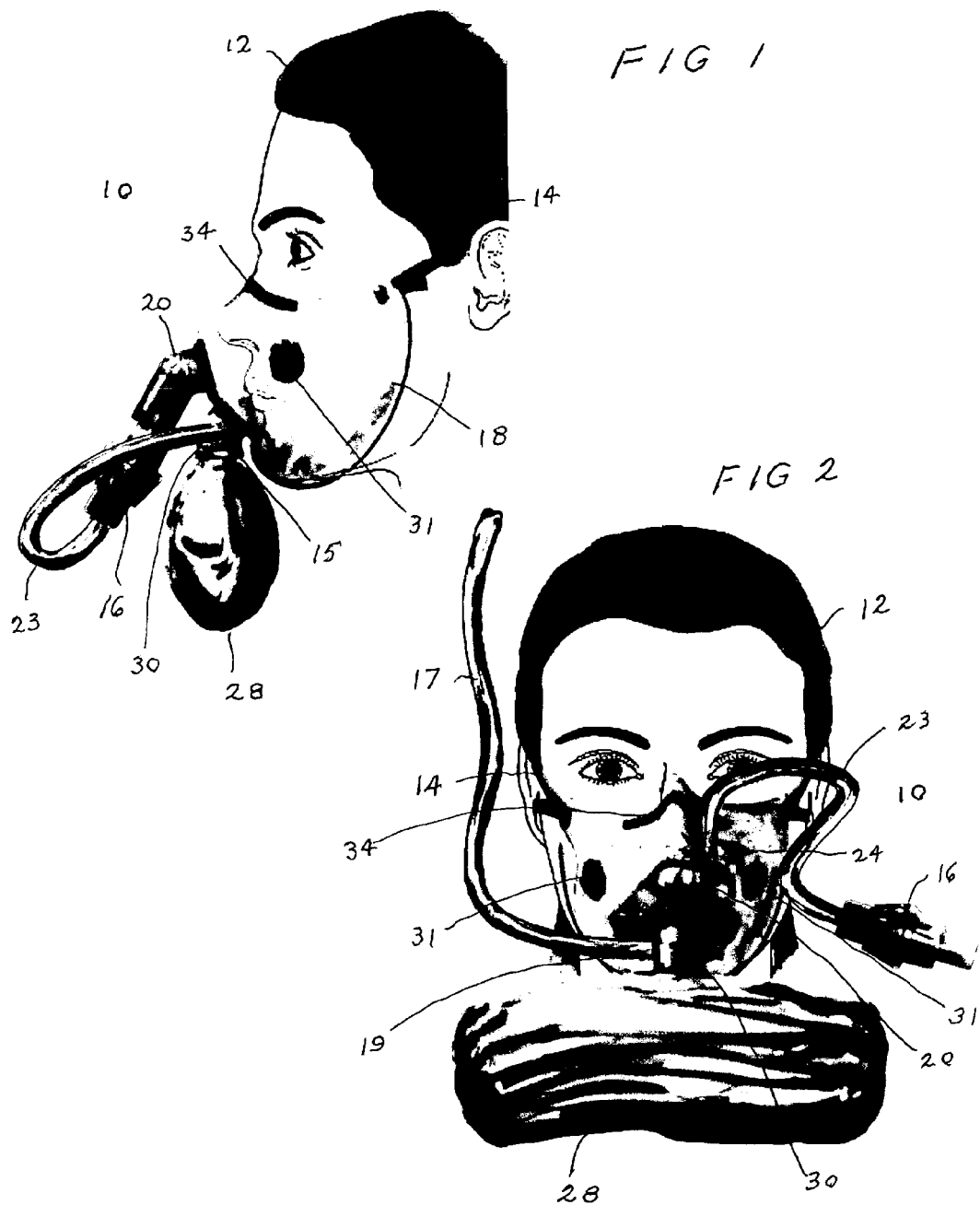

OXYGEN AND INHALATION MEDICATION DELIVERY SYSTEM

RELATED APPLICATIONS

This Application is related to and derives priority from U.S. Provisional Application No. 60/402,572, filed on Aug. 12, 2002, and which is incorporated herein by reference.

BACKGROUND

1. Field of the Invention

The present invention relates generally to oxygen delivery systems and more specifically, is concerned with an oxygen and inhalation medication therapy system.

2. Prior Art

Oxygen delivery systems have been described in the prior art; however, none of the prior art devices disclose the unique features of the present.

In U.S. Pat. No. 6,192,884,131, dated Feb. 27, 2001, Vann, et al. disclosed an apparatus and method for supplemental oxygen administration to a patient that provides enhanced efficiency of oxygen use due to the administration of an oxygen bolus at the beginning of each inhalation by a patient. The supplemental oxygen delivery device utilizes first and second one-way valves corresponding to air inspiration and air expiration ports, respectively, and that are positioned in an air pathway so that air inspiration opens the first one-way valve to permit air flow through the air inspiration port and air expiration closes the first one-way valve and opens the second one-way valve to permit air expiration through the air expiration port. An oxygen supply source is connected to the device so as to provide an air bolus in the air pathway upstream and in front of the first one-way valve so as to provide a burst of oxygen during the first part of inhalation.

In U.S. Pat. No. 6,155,258, dated Dec. 5, 2000, Voege disclosed an oxygen delivery system, which provides supplemental oxygen on demand from an oxygen source to a patient via an oxygen mask. The system includes a regulator having an inlet and an outlet. The release pin is disposed in the regulator for operation. The release pin maintains the regulator in a closed position so that the regulator prevents the flow of oxygen from the oxygen source. Upon removal of the release pin, the regulator assumes an open position so that it permits the flow of oxygen from the oxygen source, through the regulator and to the patient. The system is rechargeable and can be carried on the person or stored at home for emergency use.

While these oxygen delivery systems may be suitable for the purposes for which they were designed, they are not as suitable for the purposes of the present invention, as hereinafter described.

SUMMARY

Hereafter is disclosed, in an exemplary embodiment, a medication inhalation therapy apparatus designed for the delivery of finely misted or nebulized medicines to a patient in conjunction with the inhalation of oxygen by the patient.

A facemask equipped with an oxygen port for delivering oxygen is disclosed for placement about the face of the patient, the facemask further having a nebulizer mechanism disposed thereon which is used to deliver medication in addition to oxygen.

The nebulizer mechanism comprises a nebulizer port, which rotates 90 degrees in either direction to allow the present invention to be used in various angles. The nebulizer port is adapted to receive a nebulizer head, wherein are placed inhaleable medications, which are nebulized for delivery to, and inhalation by a patient. When the apparatus is used for medication inhalation therapy, the nebulizer head receives oxygen for nebulizing inhaleable medications placed therein, the oxygen received from an oxygen port, which delivers oxygen to the facemask. When the apparatus is not being used for medication inhalation therapy, the nebulizer head is disconnected from the oxygen port in a manner that permits the apparatus to deliver oxygen solely.

An object of the present invention, as demonstrated in the exemplary embodiment described hereafter, is to deliver medication to a patient in conjunction with the delivery of 100% oxygen.

A further object demonstrated in the exemplary embodiment is to allow the patient to receive 100% oxygen without having to reduce the patient's oxygen blood levels.

A further object, as demonstrated in the exemplary embodiment, is a medical inhalation therapy apparatus that can be used while the patient is disposed in various positions.

The foregoing and other objects and advantages will appear from the description to follow. In the description reference is made to the accompanying drawings, which form a part hereof and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense and the scope of the present invention is best defined by the appended claims.

BRIEF DESCRIPTION OF THE DRAWINGS

In order that the invention may be more fully understood, it will now be described, by way of example, with reference to the accompanying drawings in which:

FIG. 1 is a side perspective view of the present invention.

FIG. 2 is front perspective view of the present invention.

REFERENCE NUMERALS USED

Figure 3:
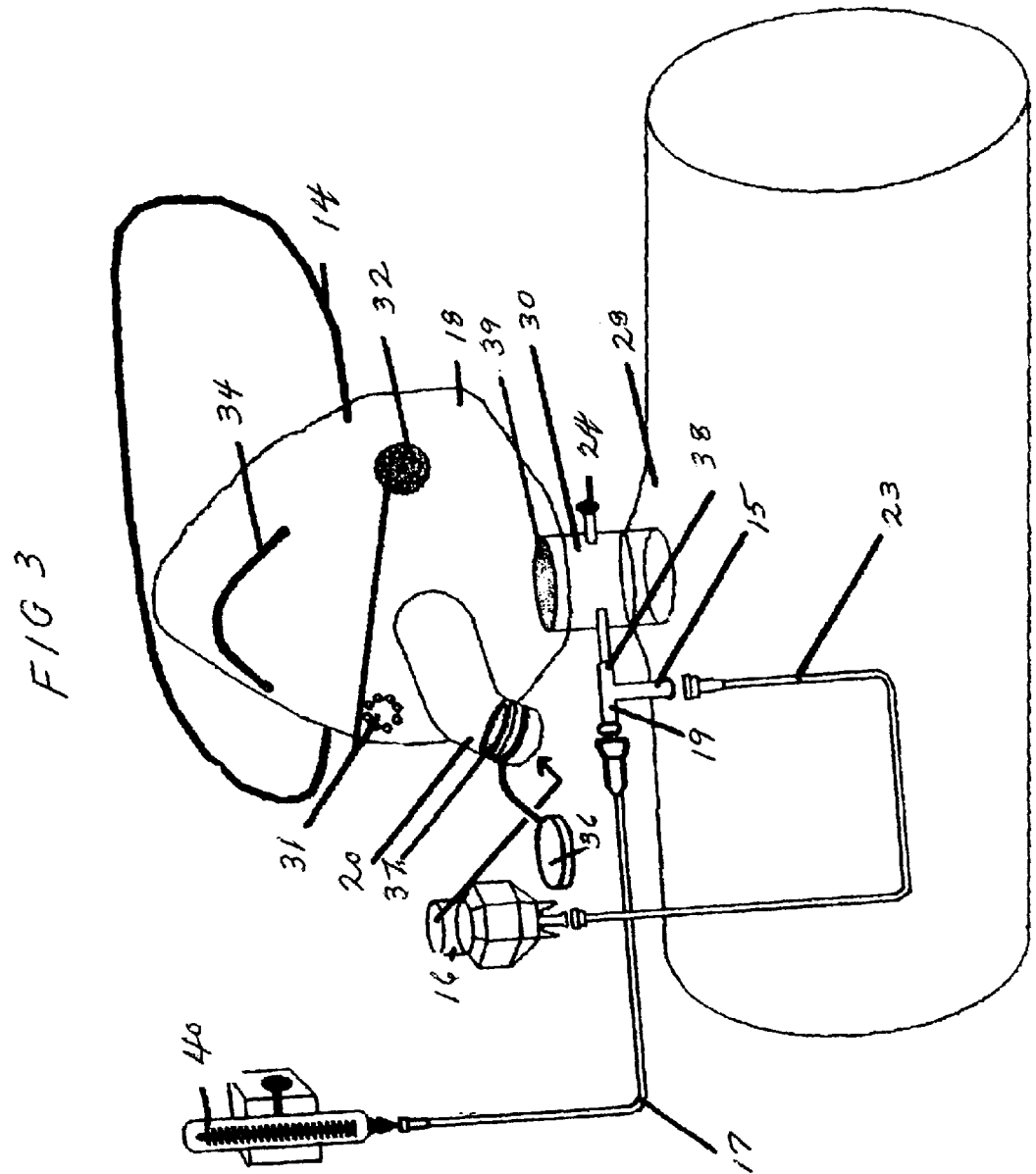
FIG. 3 shows the relationship of parts of the present invention, described in its use.

With regard to reference numerals used, the following numbering is used throughout the drawings.

10 exemplary embodiment of the present invention
12 patient
14 strap
15 diversion outlet
16 nebulizer head
18 face mask
19 oxygen inlet
20 nebulizer port
23 nebulizer-head line
24 dead nipple
28 oxygen bag
30 oxygen supply port 31 outlet for $CO_2$
32 flapper valve for $CO_2$ outlet
34 nose bridge clip
36 cap to replace nebulizer head
37 nebulizer valve
38 oxygen flow reducer
39 oxygen supply port valve
40 flow meter

DETAILED DESCRIPTION
An Exemplary Embodiment

In order that the invention may be more fully understood, it will now be described, by way of example, with reference to the accompanying drawings in which FIGS. 1 through 3 illustrate the present invention in an exemplary embodiment of the medication and oxygen-delivering system.

FIG. 1 shows a side perspective view of the exemplary embodiment 10 disposed on the face of a patient 12 wherein a strap 14 is used to hold the apparatus 10 on the face of the patient 12, and prevent oxygen and nebulized medication from escaping from the face-mask 18. Shown in FIG. 1 is a nebulizer head 16 along with a facemask 18 where the mask material may be clear, flexible plastic and where the nebulizer head 16 material is made from plastic and all fittings are molded into one piece to reduce production costs. Also shown is a rotatable nebulizer port 20, which is adapted to receive the nebulizer head 16.

The nebulizer head 16 receives oxygen for nebulizing medication from the oxygen supply port 30. The oxygen supply port 30 receives oxygen from an oxygen supply, which is metered by an oxygen flow meter 40 (shown in FIG. 3), which meters the flow of oxygen delivered to the apparatus 10 by an oxygen supply line 17 (shown in FIG. 2 and FIG. 3). The oxygen supply port 30 has a diversion outlet 15, which supplies oxygen to the nebulizer head 16, oxygen supplied through a line 23 running from the diversion outlet 15 to the nebulizer head 16. When the apparatus is not being used for inhalation therapy, the nebulizer-head line 23 is disconnected from the nebulizer head 16 and re-connected to a dead nipple 24 (shown in FIG. 2 and FIG. 3), which seals the nebulizer-head line 23, and prevents oxygen from escaping from the apparatus 10.

In a variation of the exemplary embodiment the nebulizer port 20 may be provided with a one-way valve 37 (shown in FIG. 3) to permit the one-way flow of nebulized medication into the facemask 18 for inhalation by the patient 12, and therefore to prevent backflow from the facemask 18 into the nebulizer head 16. Therefore when the nebulizer head is disconnected, the one-way valve 37 in the nebulizer port 20 prevents oxygen from flowing out the disconnected nebulizer head 16.

An exit or outlet 31 for exhaled carbon dioxide is provided in the facemask 18. The outlet 31, for example, may comprise a single hole or a plurality of holes made in the facemask. More than one exit or outlet may be made in the facemask. Also shown (in FIG. 3) is a one-way flapper outlet exhalation valve 32 for the $CO_2$ exhalation exit, along with a nose bridge clip 34. Also shown is an oxygen bag 28, which provides a reservoir of breathable oxygen.

With reference to FIG. 2, shown therein is a front perspective view of the exemplary embodiment of the present invention installed on the face of a patient 12 and held in place by strap 14. Shown in FIG. 2 is the nebulizer port 20, which is rotated 90 degrees to one side of center to allow use while the patient is lying on their side. The nebulizer port 20 is made to rotate to either side. The nebulizer-head line 23 plugs onto a dead nipple 24 when the nebulizer is not in use.

Another variant of the exemplary embodiment includes a horizontal oxygen bag 28 that keeps the same volume as standard bags but does not drape onto the patient's chest to restrict the patient in any way. The oxygen-supply line 38 supplies oxygen to the oxygen-supply port 30 from an oxygen source.

Operation

In operation, with reference to FIG. 3, the facemask 18 is placed over the mouth and nose of the patient. The strap 14 keeps the facemask tight to the patient's face, and the nose-bridge clip 34 keeps the facemask positioned properly on the patient's face. As the patient exhales, $CO_2$ passes out from beneath the facemask 18, the $CO_2$ exhaled through one or more $CO_2$ outlets 31. The facemask 18 is furnished with an appropriate number of flapper valves 32 to prevent air from entering into the facemask 18 and diluting the oxygen or medication administered to the patient.

Oxygen is delivered to the apparatus 10 at a flow rate equal to or greater than the patient's requirements in order to maintain reservoir capacity. The flow rate is controlled by a flow-meter 40, and is delivered by the oxygen supply line 17 to the oxygen supply port 30 through an oxygen flow reducer 38, as required. Oxygen flows into the facemask 18 through the oxygen supply port. The oxygen supply port may be, optionally, provided with a one-way valve 39 to prevent $CO_2$ from flowing back into the oxygen bag 28 and into the nebulizer head 16. Oxygen also flows into the bag 28, and into the nebulizer, if the nebulizer head 16 of the apparatus 10 is configured to administer medication to the patient.

When the apparatus 10 is configured to administer medication to the patient, the nebulizer head 16 is attached to the oxygen supply port 30 by means of the diversion outlet 15. The diversion outlet 15 permits oxygen flow from the oxygen supply port 30 to the nebulizer head 16 by way of the nebulizer-head line 23. Oxygen passes through the nebulizer-bead line and into the nebulizer head, where medication is nebulized. Nebulized medication flows into the nebulizer port 20, and through a one-way valve 37, as required, into the facemask 18, where the medication is inhaled with oxygen by the patient.

When the apparatus is configured so as to not deliver inhaleable medication, the nebulizer-head line 23 is disconnected from the diversion outlet 15 and connected to a dead nipple, or other means to hold the nebulizer head line. It will be appreciated that if the nebulizer port 20 is furnished with a one-way valve 37, oxygen will be prevented from flowing out of the facemask through the nebulizer port 20. If the nebulizer port 20 does not have a one-way valve, the dead nipple 24 will prevent oxygen flow out of the facemask 18 when the nebulizer-head line 23 is attached.

The patient is able to receive 100% of the oxygen and breathing medication simultaneously without compromising the patient who already is in a severe hypoxic state. The oxygen fills the reservoir then takes the path of least resistance, exits the reservoir via oxygen tubing and then over to the nebulizer. If nebulizer therapy is discontinued, the nebulizer port 20 may also be capped with the cap 36, and the nebulizer-head line 23 connected onto the dead nipple 24.

It will be appreciated the present invention allows the patient to receive the inhalation medication therapy at 100% oxygen without dropping the patient blood oxygen level. This is an improvement over the prior art, wherein during the inhalation medication delivery the patient's 100 percent oxygen delivery system is switched from 100 percent to about 35 percent oxygen for about 10–15 mi flutes and then back to the 100 percent oxygen system which can decrease the patient's blood oxygen level.

I claim:

1. A medical inhalation apparatus for dispensing medication and high concentrated oxygen to a patient, the apparatus comprising
   a facemask for delivering oxygen and medication to be inhaled by the patient, the facemask having a first opening for expelling carbon dioxide;
   an oxygen supply port, the oxygen supply port attached to the facemask and adapted to transfer oxygen to the facemask, the oxygen supply port receiving oxygen from an attached line, the oxygen supply port further having a diversion outlet for carrying oxygen away from the oxygen supply port;
   a nebulizer port attached to the facemask, the nebulizer port adapted to transfer nebulized materials into the facemask, the nebulizer port having a removable nebulizer-head holding inhaleable medication for nebulizing, the nebulizer-head receiving oxygen from the diversion outlet and nebulizing medication into the facemask to be inhaled by the patient; and
   an oxygen bag attached the oxygen supply port, the oxygen bag exchanging oxygen with the oxygen supply port;
   wherein the flow of oxygen into the nebulizer-head nebulizes inhaleable medication, the opening expels carbon dioxide exhaled by the patient and the patient breathes high concentrated oxygen and inhaleable medication.

2. The apparatus of claim 1, wherein the nebulizer port is rotatable.

3. The apparatus of claim 1, wherein the oxygen supply port has a reducer for reducing oxygen flow from the attached line into the oxygen supply port.

4. The apparatus of claim 1, wherein the facemask has a second opening for expelling carbon dioxide, carbon dioxide expelled through a one-way valve in the second opening.

5. The apparatus of claim 4, wherein the second opening is comprised of a plurality of holes, and the one-way valve permits carbon dioxide to flow out of the facemask through the plurality of holes.

6. The apparatus of claim 1, wherein the oxygen bag is a horizontal bag.

7. The apparatus of claim 1, wherein the oxygen supply port has an inlet, the inlet having a first branch and a second branch, the first branch having a reducer for reducing oxygen flow in the line attached to the first branch, and the second branch serving as the diversion outlet.

8. The apparatus of claim 1, wherein the nebulizer-head receives oxygen from the diversion outlet by a disconnectable nebulizer-head line, whereby the nebulizer-head line is disconnected from the nebulizer-head.

9. The apparatus of claim 8, wherein the oxygen supply port has a dead nipple for receiving the nebulizer-head line disconnected from the nebulizer-head, whereby the nebulizer-head line is connected to the dead nipple preventing oxygen flow out of the nebulizer-head line.

10. The apparatus of claim 9, further including a cap for sealing the nebulizer port, and wherein the nebulizer-head is removed from the nebulizer port and the nebulizer port is sealed with the cap.

11. The apparatus of claim 1, the nebulizer port further including a one-way valve to permit one-way flow of gases from the nebulizer port into the facemask.

12. The apparatus of claim 1, wherein the first opening is comprised of a plurality of holes.

13. The apparatus of claim 1, wherein the nebulizer port has a one-way valve for transferring inhaleable medication into the facemask.

14. A method for dispensing medication and high concentrated oxygen to a patient, the method comprising
   providing a facemask for delivering oxygen and medication to be inhaled by the patient, the facemask having a first opening for expelling carbon dioxide;
   providing an oxygen supply port, wherein the oxygen supply port is adapted to transfer oxygen to the facemask, the oxygen supply port receiving oxygen from an attached line, the oxygen supply port further having a diversion outlet for carrying oxygen away from the supply port;
   attaching the oxygen supply port to the facemask;
   providing a nebulizer port, the nebulizer port adapted to transfer nebulized materials into the facemask through a one-way valve in the nebulizer port, the nebulizer port having a removable nebulizer-head holding inhaleable medication for nebulizing, the nebulizer-head receiving oxygen from the diversion outlet and nebulizing medication into the facemask to be inhaled by the patient;
   attaching the nebulizer port to the facemask;
   providing an oxygen bag, the oxygen bag exchanging oxygen with the oxygen supply port;
   attaching the oxygen bag to the oxygen supply port; and
   placing the facemask over the patients nose and mouth;
   whereby the flow of oxygen into the nebulizer-head nebulizes inhaleable medication, the opening expels carbon dioxide exhaled by the patient and the patient breathes high concentrated oxygen and inhaleable medication.

15. The method of claim 14, wherein the nebulizer port is rotatable when attached to the facemask.

16. The method of claim 14, wherein the oxygen bag is a horizontal bag.

17. The method of claim 15, wherein the patient is laying on the patient's side, and the nebulizer port is rotated, whereby the inhaleable medication is maintained properly for nebulizing.

18. The method of claim 16, wherein the patient is covered by bedding, whereby the oxygen bag is not collapsed by the bedding.

19. A method for dispensing inhaleable medication and high concentrated oxygen to a patient, the method comprising:
   providing an apparatus, the apparatus comprising:
      a facemask for delivering oxygen and medication to be inhaled by the patient, the facemask having a first opening for expelling carbon dioxide;
      an oxygen supply port, the oxygen supply port attached to the facemask and adapted to transfer oxygen to the facemask, the oxygen supply port receiving oxygen from an attached line, the oxygen supply port further having a diversion outlet for carrying oxygen away from the supply port;
      a nebulizer port attached to the facemask, the nebulizer port adapted to transfer nebulized materials into the facemask, the nebulizer port having a removable nebulizer-head holding inhaleable medication for nebulizing, the nebulizer-head receiving oxygen from the diversion outlet and nebulizing medication into the facemask to be inhaled by the patient; and
      an oxygen bag attached the oxygen supply port, the oxygen bag exchanging oxygen with the oxygen supply port;
   placing the facemask over the patients nose and mouth;
   whereby the flow of oxygen into the nebulizer-head nebulizes inhaleable medication, the opening expels carbon dioxide exhaled by the patient and the patient breathes high concentrated oxygen and inhaleable medication.

* * * * *